US00PP10197P

United States Patent [19]

VandenBerg

[11] Patent Number: Plant 10,197

[45] Date of Patent: Jan. 13, 1998

[54] CHRYSANTHEMUM PLANT NAMED 'OMAHA'

[75] Inventor: Cornelis P. VandenBerg, Salinas, Calif.

[73] Assignee: Yoder Brothers Inc., Barberton, Ohio

[21] Appl. No.: 709,748

[22] Filed: Sep. 9, 1996

[51] Int. Cl.[6] ..... A01H 5/00

[52] U.S. Cl. ..... Plt./82.5

[58] Field of Search ..... Plt./74.1, 82.5

*Primary Examiner*—Howard J. Locker

*Attorney, Agent, or Firm*—C. A. Whealy

[57] ABSTRACT

A distinct cultivar of Chrysanthemum plant named 'Omaha', characterized by its medium sized anemone-type inflorescences; attractive red ray florets and golden disc florets; numerous inflorescences per plant; and excellent postproduction longevity.

3 Drawing Sheets

1

The present invention relates to a new and distinct cultivar of Chrysanthemum plant, botanically known as *Dendranthema grandiflora* and referred to by the cultivar name Omaha.

The new cultivar is a product of a planned breeding program conducted by the inventor in Salinas, Calif. The objects of the breeding program is to create new Chrysanthemum cultivars having inflorescences with desirable colors and good form and substance.

The new cultivar originated from a cross made by the inventor in May, 1991, of two unnamed proprietary seedling selections. The female parent, seedling number 0053, had single-type dark pink inflorescences. The male parent, seedling number 0041, had anemone-type pink purple inflorescences.

The cultivar Omaha was discovered and selected by the inventor as a flowering plant within the progeny of the stated cross in a controlled environment in Alva, Fla., in January, 1993. The selection of this plant was based on its desirable inflorescence color and good form and substance.

Asexual reproduction of the new cultivar by terminal cuttings taken in a controlled environment in Alva, Fla., has shown that the unique features of this new Chrysanthemum are stable and reproduced true to type in successive generations.

The cultivar Omaha has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Omaha'. These characteristics in combination distinguish 'Omaha' as a new and distinct cultivar:

1. Medium sized anemone-type inflorescences that are about 8 cm in diameter.
2. Attractive red ray florets and golden disc florets.
3. Numerous inflorescences per plant.
4. Excellent postproduction longevity with inflorescences maintaining good substance and color for about four weeks in an interior environment after one week of cool storage.

The new Chrysanthemum is similar in ray floret color to the Chrysanthemum cultivar Foxy (disclosed in U.S. Plant Pat. No. 5,414). However in side-by-side comparisons in Salinas, Calif., under commercial practice, plants of the new Chrysanthemum have anemone-type inflorescences whereas plants of the cultivar Foxy have daisy-type inflorescences. Additionally, plants of the new Chrysanthemum are taller than plants of the cultivar Foxy.

2

The accompanying colored photographs illustrate the overall appearance of the new cultivar, showing the colors as true as it is reasonably possible to obtain in colored reproductions of this type.

The first photograph comprises a side perspective view of a typical flowering stem of 'Omaha' grown as a single stem spray cut chrysanthemum.

The second photograph comprises a top perspective view of inflorescences of the cultivar Omaha at three different stages of development: unopened inflorescence, opening inflorescence, and fully opened inflorescence.

The third photograph comprises a top perspective view of the adaxial surface of leaves of the cultivar Omaha at three different stages of development showing the differences in size and lobation development. Floret and foliage colors in the photographs may differ from the actual colors due to light reflectance.

In the following description, color references are made to The Royal Horticultural Society Colour Chart except where general terms of ordinary dictionary significance are used. The following observations and measurements describe plants grown in Salinas, Calif., under commercial practice in a polyethylene-covered greenhouse with night temperatures ranging from 15 to 17C, day temperatures up to 24C, and light levels of 2,500 to 3,000 footcandles. After planting rooted cuttings of the new cultivar, plants received 11 long day/short nights following by short day/long nights until flowering. Measurements and numerical values represent averages for six typical flowering stems.

Botanical classification: *Dendranthema grandiflora* cultivar Omaha.

Commercial classification: Anemone spray-type cut chrysanthemum.

Parentage:

*Male or pollen parent.*—Unnamed proprietary Denranthema grandiflora seedling selection number 0041.

*Female or seed parent.*—Unnamed proprietary Dendranthema grandiflora seedling selection number 0053.

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous anemone spray-type cut flower. Stems upright, uniform habit and freely branching.

*Flowering stem length.*—99 to 112 cm.

*Foliage description.*—Leaf arrangement: Alternate. Leaf size, fully expanded: Length: About 9.5 cm. Width: About 6 cm. Leaf apex: Acuminate. Leaf base: Attenuate. Leaf margin: Palmately lobed. Leaf texture: Abaxial and adaxial surfaces slightly pubescent. Veins prominent on abaxial surface. Color: Young foliage adaxial surface: 147A. Young foliage abaxial surface: 147B. Mature foliage adaxial surface: 147A. Mature foliage abaxial surface: 147B. Venation adaxial surface: 147B. Venation abaxial surface: 147B. Petiole: Length: About 2 cm. Color: 147A.

Flowering description:

*Appearance.*—Anemone-type inflorescence form. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to 1.5 to 2 weeks of long day/short night conditions after planting followed by photoinductive short day/long night conditions flowers about 56 to 59 days later.

*Postproduction longevity.*—In an interior environment, inflorescences of our flowering stems will maintain good color and substance for about four weeks in an interior environment after one week of cool storage.

*Quantity of Inflorescences.*—About 13 inflorescences per flowering stem.

*Inflorescence size.*—Diameter: About 8 cm. Depth (height): About 1.5 cm. Diameter of disc: About 2.2 cm.

*Ray florets.*—Shape: Elongated, narrow. Size: Length: About 3.75 cm. Width: About 1.1 cm. Apex: Acute to rounded. Base: Acute. Margin: Entire. Texture: Satiny, smooth, glabrous, ribbed lengthwise. Aspect: Flat to slightly twisted. Number of ray florets per inflorescence: About 52. Color: When opening: Adaxial surface: 46A. Abaxial surface: 46A/46B. Mature: Adaxial surface: 46A, color does not fade with further development. Abaxial surface: 182B with longitudinal streaks of 182A, color does not fade with further development.

*Disc florets.*—Shape: Enlarged tubular. Size: Length: About 1.3 cm. Width: Base: About 3 mm. Top: About 1 1 mm. Number of disc florets per inflorescence: About 183. Color: Immature: 154A. Mature: Tube: Tip: 15B, translucent to red throat. Mid-section: 3A. Base: Greenish white. Throat: Tip: 46A. Mid-section: 3A. Base: White.

*Peduncle.*—Aspect: Strong and angled about 40° to the stem. Length: First peduncle: About 11 cm. Fourth peduncle: About 16.5 cm. Seventh peduncle: About 21.5 cm. Texture: Glabrous. Color: 147B.

*Reproductive organs.*—Androecium: Present on disc florets only. Anther color: 13A. Pollen: Moderate, 13A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Omaha', as illustrated and described.

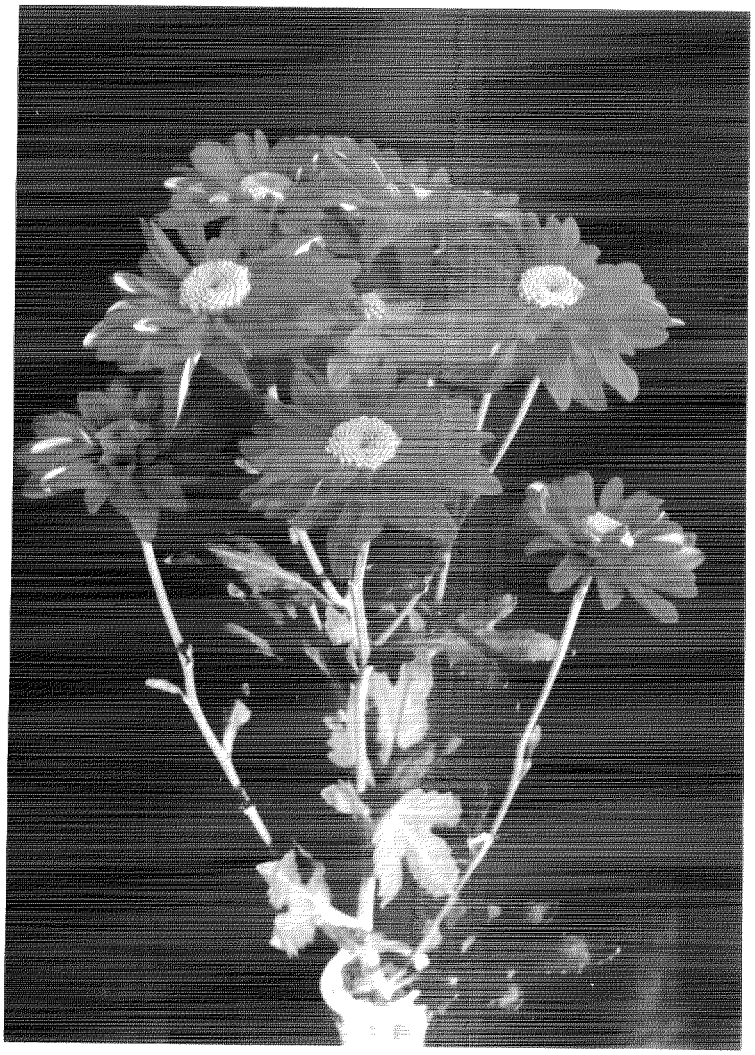

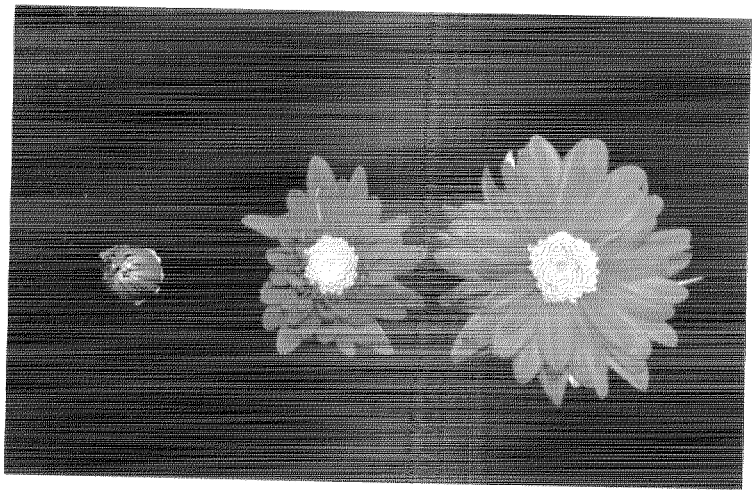

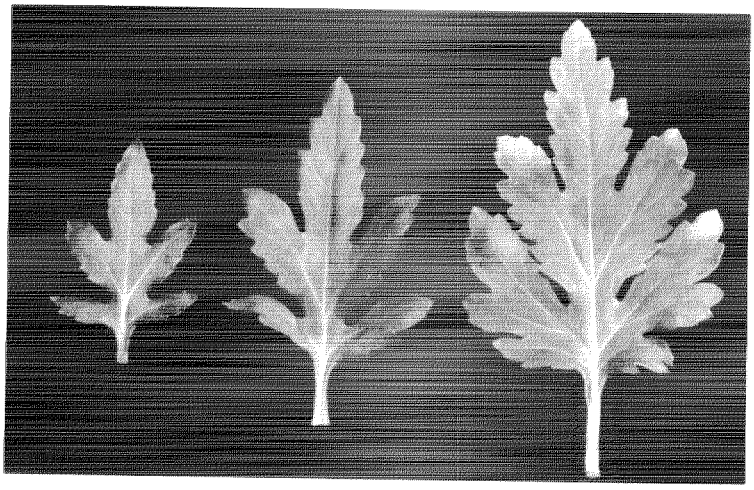

* * * * *